United States Patent [19]

Wright et al.

[11] 4,122,082
[45] Oct. 24, 1978

[54] 4-DESACETOXY-4-OXOVINBLASTINE

[75] Inventors: Ian G. Wright, Greenwood; Norbert Neuss, Indianapolis, both of Ind.

[73] Assignee: Eli Lilly and Company, Indianapolis, Ind.

[21] Appl. No.: 848,837

[22] Filed: Nov. 7, 1977

[51] Int. Cl.$^2$ .......................................... C07D 519/04
[52] U.S. Cl. .................................. 260/287 B; 424/258
[58] Field of Search .................................... 260/287 B

[56] References Cited

PUBLICATIONS

Albright et al., J. Org. chem. 30, 1107 (1965).

*Primary Examiner*—Donald G. Daus
*Assistant Examiner*—David E. Wheeler
*Attorney, Agent, or Firm*—James Lincoln Rowe; Everet F. Smith

[57] ABSTRACT

4-Desacetoxy-4-oxovinblastine, prepared by oxidation of 4-desacetylvinblastine, useful as an intermediate.

2 Claims, No Drawings

4-DESACETOXY-4-OXOVINBLASTINE

BACKGROUND OF THE INVENTION

The vinca alkaloids, a group of dimeric indoledihydroindoles, have achieved considerable prominence as marketed or experimental chemotherapeutic drugs for the treatment of susceptible carcinomas, sarcomas, and leukemias. These agents are used both alone and in combination with other oncolytic agents. As a class, the vinca alkaloids include compounds obtainable from the leaves of *vinca rosea,* derivatives produced by chemical modification thereof and more recently, dimeric alkaloids produced by coupling two "monomeric" indoles via a modified Polonovski reaction — see Langlois and Potier, *Tetrehedron Letters,* 1099 (1976), Potier, et al., *J.C.S. Chem. Comm.,* 670 (1975), Kutney et al., *Heterocycles,* 3, 205 (1975) and Atta-ur-Rahman, *Tetrahedron Letters,* 2351 (1976).

A majority of the known vinca alkaloids can be represented by the following formula:

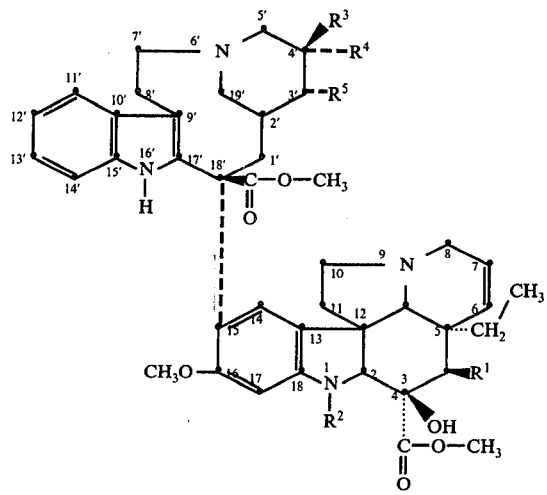

In the above formula where $R^1$ is acetoxy, $R^2$ is methyl, $R^3$ is hydroxyl, $R^4$ is ethyl and $R^5$ is H, vinblastine is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" (4'-deoxyvinblastine) but where $R^3$ is ethyl and $R^4$ is hydrogen, deoxy VLB "B" (4'-deoxyleurosidine) is represented; where $R^1$ is acetoxy, $R^2$ is methyl, $R^3$ is ethyl and $R^4$ and $R^5$ taken together form an α-epoxide ring, leurosine is represented; and where $R^1$, $R^3$, $R^4$ and $R^5$ are the same as in leurosine but $R^2$ is formyl, leuroformine (N-formylleurosine) is represented.

The above-mentioned alkaloids are described in the following publications: leurosine (vinleurosine — U.S. Pat. No. 3,370,057), VLB (vincaleukoblastine, vinblastine — U.S. Pat. No. 3,097,137), leurosidine (vinrosidine) and vincristine (leurocristine or VCR) (both in U.S. Pat. No. 3,205,220), and deoxy VLB "A" and "B," *Tetrahedron Letters,* 783 (1958). Other alkaloids obtainable from vinca rosea include 4-desacetoxy vinblastine (U.S. Pat. No. 3,954,773); 4-desacetoxy-3'-hydroxyvinblastine (U.S. Pat. No. 3,944,554); leurocolombine (2'-hydroxy VLB — U.S. Pat. No. 3,890,325) and vincadioline (3'-hydroxy VLB — U.S. Pat. No. 3,887,565).

Two of the above alkaloids, VLB and vincristine, are now marketed as drugs for the treatment of malignancies, particularly the leukemias and related diseases in humans. Of these marketed compounds, vincristine is a most active and useful agent in the treatment of leukemias but is also the least abundant of the antineoplastic alkaloids of *Vinca rosea.* Jovanovics et al. — U.S. Pat. No. 3,899,493 — have developed an elegant oxidative procedure for converting the more abundant alkaloid VLB to vincristine employing chromic acid in acetone and acetic acid at about −60° C. The same procedure has been used to prepare leuroformine (N-formylleurosine) from leurosine — see Belgian Pat. No. 811,110. Leuroformine is currently undergoing a clinical trial in Europe, chiefly in treatment of the leukemias and of multiple myeloma.

Chemical modification of VLB and vincristine has centered around hydrolysis of the 4-acetoxy group to yield 4-desacetyl VLB (DAVLB) or 4-desacetylvincristine (DAVCR) followed by reesterification with other acyl and amino-acyl groups — see U.S. Pat. Nos. 3,392,173 and 3,387,001—, or replacement of the C-3 ester function by an amide function — see Belgian Pat. No. 837,390. One of the former 4-acyl derivatives, the 4-N,N-dimethylglycine ester underwent a brief clinical trial and one of the latter, vindesine, (4-desacetyl VLB C-3 carboxamide) is currently being tested clinically against a variety of neoplasms.

Other chemical modification of the VLB molecule such as hydrolysis and decarboxylation of the C-18' carbomethoxy group has resulted in a loss of anti-cancer activity as has the formation of N-oxides; i.e., pleurosine (leurosine N-oxide). Oxidative attack on VLB under temperatures higher than −60° C. or in neutral or basic solution has resulted in the formation of a chemotherapeutically inactive compound, vinamidine, represented by the following formula:

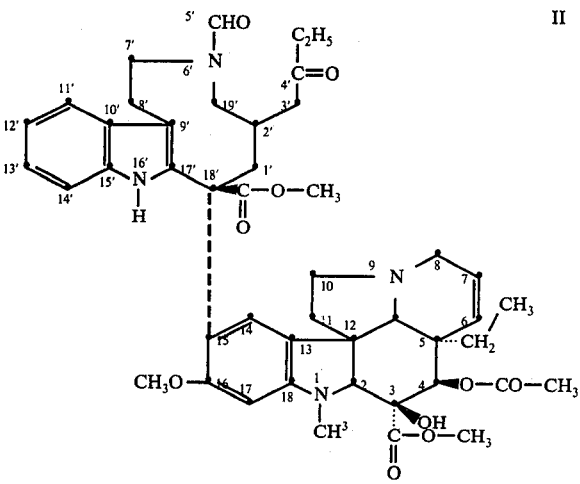

Oxidation of VLB with $MnO_2$ in acetone or $CH_2Cl_2$ at ambient temperature has also yielded vinamidine. The same alkaloid has been encountered in alkaloidal fractions from *Vinca rosea* leaves — see Tafur et al. *J. Pharm. Sci.,* 64, 1953 (1975) — but the structure assigned therein (II on page 1956) is now believed to be incorrect and the above structure more closely represents the NMR, IR, and mass spectral data obtained from physiochemical studies of the compound. Vinamidine may arise from oxidative attack on VLB in which a vincinal 4',5'-dihydroxy derivative is formed which glycol, upon further oxidation, splits between the hydroxyls(4',5'bond) to yield a ring-opened derivative such as II above.

4-Desacetyl VLB and other 4-desacetyl compounds; i.e., those in which $R^1$ in Formula I is hydroxyl, are not oxidized to the corresponding 4-oxo derivative by the Jovanovics low-temperature chronic acid oxidation (see Cullinan — Ser. No. 723,350). Theoretical considerations emphasize the difficulty of oxidizing the secondary hydroxyl at C-4 to a carbonyl. The ring containing the C-4 carbon is locked into position since four of the ring carbons are fused into other rings of the vindoline portion of the molecule. In order to undergo oxidation from a secondary hydroxyl to a carbonyl, the bond angles of the C-4 carbon would have to change from the tetrahedral angle (108°) to the $sp^2$ angle (120°). Such a change in the fused ring environment in which the C-4 carbon finds itself would involve considerable ring strain.

It is an object of this invention to provide 4-oxo derivatives of selected 4-desacetyl vinca alkaloids utilizing oxidizing agents which are effective to oxidize the secondary alcohol at C-4 without also oxidizing the velbanamine portion of the molecule to yield a vinamidine type derivative.

SUMMARY OF THE INVENTION

In fullfillment of the above and other objects, this invention provides dimeric indole-dihydroindole alkaloids of the formula:

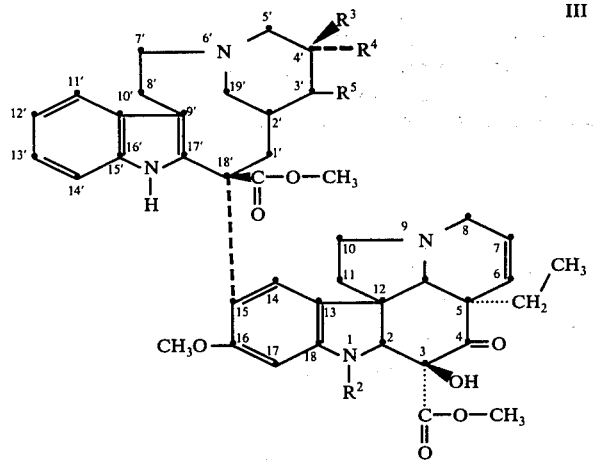

wherein $R^2$ is $CH_3$ or CHO, and, when taken singly, $R^5$ is H and one of $R^3$ and $R^4$ is OH or H and the other is $C_2H_5$ and when $R^4$ and $R^5$ are taken together they form an α-epoxide ring and $R^3$ is $C_2H_5$.

Also included within the scope of this invention are the pharmaceutically acceptable acid addition salts of the above alkaloidal bases including salts derived from inorganic acids such as: hydrochloric acid, nitric acid, phosphoric acid, sulfuric acid, hydrobromic acid, hydriodic acid, nitrous acid, phosphorus acid and the like, as well as salts of organic acids including aliphatic mono and dicarboxylic acids, phenyl-substituted alkanoic acids hydroxy alkanoic and alkandioic acids, aromatic acids, aliphatic and aromatic sulfonic acids, etc. Such pharmaceutically acceptable salts thus include the sulfate pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

The alkaloidal bases of this invention are prepared by oxidizing a 4-desacetyl (or C-4 hydroxy) compound of the formula

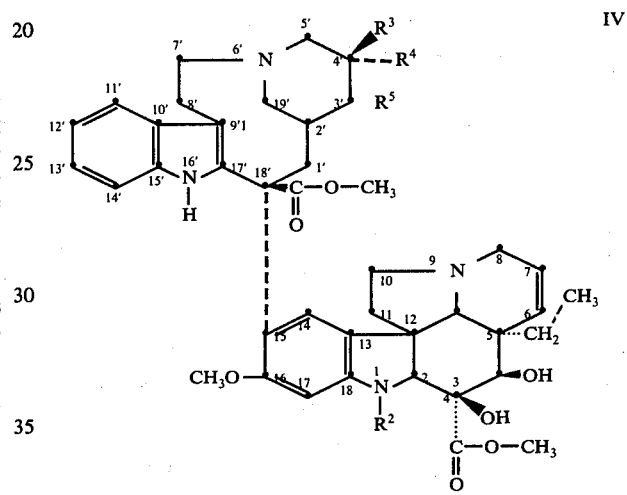

wherein $R^2$, $R^3$, $R^4$ and $R^5$ have the same meaning as hereinabove, with Moffat's Reagent — dimethyl-sulfoxide (DMSO), dicyclohexylcarbodiimide (DCC) and ortho phosphoric acid or other similar oxidizing agents. This reagent was originated by Pfitzner and Moffat, *J. Am. Chem. Soc.*, 85, 3027 (1963) 87 5661, 5670 (1965) — see also Fieser and Fieser, *Reagents for Organic Synthesis*, 1, 304, 2 162 (John Wiley and Sons, Inc., 1967).

In carrying out the synthesis of the 4-oxo compounds (Formula III) of this invention with Moffat's reagent a 4β-hydroxy compound of Formula IV (as the free base) and the dicyclohexylcarbodiimide are dissolved in DMSO at room temperature and the phosphoric acid is then added. The reaction mixture is agitated until solution is complete (5–10 minutes). The reaction flask is then stoppered and allowed to remain at room temperature until the reaction is substantially complete — 5 to 6 hours — as shown by TLC analysis of aliquot samples worked up by standard procedures. The desired product is isolated by diluting the reaction product with dilute sulfuric acid, filtering the resulting mixture and washing the precipitated dicyclohexylurea with 1 percent aqueous sulfuric acid. The filtrate is made basic with 14 N aqueous ammonium hydroxide and extracted into a water immiscible organic solvent such as methylene dichloride or ether. The organic extracts are combined, dried, and the solvent removed by evaporation. The residue containing the desired 4-oxo compound is purified by chromatography, gradient elution chromatography, or gradient pH extraction. The latter procedure is preferred.

In carrying out the above-mentioned oxidation employing Moffat's Reagent, it is customary to use an excess of the reagent. For example, an excess of dicyclohexylcarbodiimide of 2-10 fold and a 2 to 5 fold excess of ortho phosphoric acid are employed. Dimethylsulfoxide is used as both a reactant and a solvent and it is therefore, always in a 10 to 20 fold excess. It is preferred to employ a 6-7 molar excess of dicyclohexylcarbodiimide and a 2.5 to 3 molar excess of ortho phosphoric acid per mole of starting material. The reaction can be carried out at temperatures ranging from 20° C. to 50° C., but it is preferred to employ temperature of about 20° C. As would be expected, the higher the temperature, the faster the reaction. However, temperatures in excess of about 25° C. may give rise to excessive quantities of decomposition products. On the other hand, the reaction does not go rapidly to completion at 20° C. and time periods of from 5 to 7 hours are needed for substantial completion of the oxidation procedure. Longer periods of time will, of course, be necessary if lower reaction temperatures are employed.

An alternative oxidizing agent is the combination of N-chlorosuccinimide and dimethylsulfide, used in conjunction with a tertiary amine such as triethylamine. Other equally useful oxidizing agents will readily suggest themselves to these skilled in the art.

Compounds according to Formula III wherein $R^2$ is CHO can be prepared by low temperature oxidation of the corresponding compound wherein $R^2$ is $CH_3$ by the procedure of Jovanovics et al., U.S. Pat. No. 3,899,493.

The starting materials useful to prepare the compounds of this invention — those materials represented by IV above — are prepared by hydrolysis of the corresponding acetates, (the hydroxyl at C-4 in Formula IV is acetylated). Compounds according to IV in which $R^2$ is $CH_3$ and the C-4 hydroxyl is acetylated are known compounds; i.e., vinblastine is disclosed in U.S. Pat. No. 3,097,137, leurosidine in U.S. Pat. No. 3,205,220, leurosine, in U.S. Pat. No. 3,370,057 and deoxy VLB "A" and "B" in *Tetrahedron Letters,* 783 (1958). The corresponding compounds in which $R^2$ is CHO are also known and include vincristine, also disclosed in U.S. Pat. No. 3,205,220, leuroformine, Belgian Pat. No. 881,110, 4'-deoxyvincristine and 4'-deoxy-1-formylleurosidine in the copending application of Gerald L. Thompson, Ser. No. 760,595, filed Jan. 19, 1977. The remaining compound, 1-desmethyl-1-formylleurosidine is prepared by the low temperature oxidation of leurosidine with chromic oxide according to the procedure of U.S. Pat. No. 3,899,493. The corresponding 4-desacetyl compounds are prepared from the above vinca alkaloids by hydrolysis either under acidic or basic conditions. Hargrove, *Lloydia,* 27, 340, (1964) first prepared 4-desacetyl vinblastine by the acidic hydrolysis of vinblastine using large volumes of absolute methanol saturated at 0° C. with anhydrous hydrogen chloride. A contact time of about 6 hours was used. Acidic hydrolysis also seems to be the procedure of choice for preparing 4-desacetyl deoxy VLB "B" and "A." However, it has been found that an alkaline hydrolysis procedure is preferred for the preparation of 4-desacetyl derivatives of both leurosine and vinblastine. According to this procedure, sodium carbonate in refluxing methanol is employed as the hydrolytic medium.

This invention is further illustrated by the following specific examples.

EXAMPLE 1

4-Desacetoxy-4-oxovinblastine

A reaction mixture was prepared by adding 3.0739 g. of 4-desacetylvinblastine and 5.8929 g. of dicyclohexylcarbodiimide to 20 ml. of DMSO. 1.2185 Grams of ortho phosphoric acid (anhydrous) dissolved in 5 ml. DMSO were added. The reaction flask was stoppered and swirled until solution was complete. The reaction mixture was maintained at ambient temperature (18°-22° C.) for 5 hours, and was then poured into a mixture of ice and 1% aqueous sulfuric acid. The precipitated dicyclohexylurea was removed by filtration and the filter cake washed with 1% aqueous sulfuric acid. The aqueous layer was made basic with 14 N aqueous ammonium hydroxide. This aqueous alkaline mixture was extracted several times with methylene dichloride. The methylene dichloride extracts were combined and dried and the solvent removed therefrom by evaporation in vacuo leaving a residue containing 4-desacetoxy-4-oxovinblastine (2.6534 g.). The residue was dissolved in 1% aqueous sulfuric acid, the resulting solution filtered, and the filtrate made basic with 14 N $NH_4OH$ as before. Extraction with $CH_2Cl_2$ followed by drying and removal of the solvent yielded a residue. Thin-layer chromatography of an aliquot over silica gel using a 1:1 ethyl acetate/ethanol solvent mixture showed the residue to consist of essentially one-spot material. The residue was combined with 298 mg. of a similar residue from a chromatographic separation procedure in a previous run, and the combined material dissolved in 400 ml. of a 0.1 M citric acid buffer, (pH = 2.35) and subjected to a gradient pH extraction procedure. The acidic solution was extracted with 400 ml. of benzene and the pH adjusted to 3.0. The solution was again extracted with 400 ml. of benzene, the pH raised again, etc. The following chart gives the pH of the solution in column 1 and in column 2, the weight of material in the fraction after removal of the benzene. Each fraction was analyzed by thin-layer chromatography as before for the presence of 4-desacetoxy-4-oxovinblastine.

Table 1

| pH of aqueous layer | weight in mg. of extracted product | |
|---|---|---|
| 2.35 | 205.8 | (discarded) |
| 3.0 | 167.1 | |
| 3.5 | 270.6 | |
| 4.0 | 671.4 | (combined) |
| 4.5 | 740.1 | |
| 5.0 | 257.7 | |
| 5.5 | 123.0 | |
| 6.0 | 66.7 | |
| 6.5 | 26.7 | |
| 7.0 | 23.8 | |
| 7.5 | 12.8 | (discarded) |
| 8.0 | 22.7 | |
| 9.0 | 17.8 | |

Fractions taken at pH 3.0–5.0 were combined with a filtrate from a crystallization of 4-desacetoxy-4-oxovinblastine obtained previously by chromatography, and the combined fractions dissolved in 400 ml. of 0.1 m citric acid buffer as before. A second gradient pH extraction procedure was carried out as above except that, in some instances, more than one extraction with a 400 ml. portion of benzene was carried out. Table 2 gives the results of this extraction procedure. Column 1 gives the pH of the aqueous layer, Column 2 the number of extractions with 400 ml. portions of benzene, and Column 3, the weight in milligrams of extracted product after evaporation of the solvent.

Table 2

| pH of aqueous layer | no. of extractions | weight in mg. of extracted product | |
|---|---|---|---|
| 2.35 | 3 | 252.4 | (discarded) |
| 2.75 | 2 | 97.1 | |
| 3.15 | 1 | 114.2 | |
| 3.55 | 1 | 276.1 | |
| 4.00 | 3 | 1154.2 | |
| 4.5 | 1 | 213.2 | |
| 5.0 | 1 | 89.7 | |
| 5.5 | 1 | 32.2 | |
| 6.0 | 1 | 18.7 | |
| 8.0 | 1 | 13.5 | |

The fraction at pH = 4.0 weighing 1.1542 g. was crystallized from a methanol/water mixture. 854.3 Milligrams of crystalline 4-desacetoxy-4-oxovinblastine were obtained. Infrared and NMR spectra were in accordance with the proposed structure.

EXAMPLE 2

Alternate Preparation of 4-Desacetoxy-4-oxovinblastine

A solution was prepared containing 2.47 g. of 4-desacetylvinblastine in 37 ml. of toluene and 7.4 ml. of methylene dichloride. 1.29 Grams of N-chlorosuccinimide were suspended in 30 ml. of anhydrous toluene and the suspension stirred under a nitrogen atmosphere with cooling. 1.06 Milliliters (0.9 g.) of dimethylsulfide were added to this suspension in dropwise fashion. The mixture was then stirred for an additional 15 minutes. Next, the solution of the 4-desacetylvinblastine was added in dropwise fashion over a period of 5 minutes at 0° C. to the mixture of N-chlorosuccinimide and dimethylsulfide in toluene. (The following volumes of solvents were used: 15 times weight of starting material for toluene on a weight/volume basis, 3 times weight of starting material on a weight/volume basis of starting material for N-chlorosuccinimide and an excess of dimethylsulfide. After stirring for 5.6 hours at 0° C., 2.02 ml. (1.47 g.) of triethylamine were added and the reaction mixture was stirred for an additional one-half hour at room temperature and then stored overnight in the refrigerator. Thin-layer chromatography indicated that all of the starting material, 4-desacetylvinblastine, had been consumed, and that the reaction mixture consisted essentially of single spot material. The reaction mixture was diluted with ether plus methylene dichloride and the resulting organic layer washed three times with water and then dried. Removal of the solvents in vacuo yielded a yellow solid comprising 4-desacetoxy-4-oxovinblastine; weight = 2.39 g. This material was chromatographed over 240 g. of activity I silica. The chromatogram was developed with 400 ml. portions of 1:1 methylene dichloride/ethyl acetate containing 9, 13.5, 20, 30, and 45 percent added methanol. After 700 ml. of eluent had been collected, 20 ml. fractions were then taken. Fractions 21–45 yielded, when combined and the solvents evaporated, 1.28 g. of a tan solid, 4-desacetoxy-4-oxovinblastine.

4-Oxo-4-desacetoxyleurosidine, 4-oxo-4-desacetoxyvincristine, 4-oxo-4-desacetoxy-1-desmethyl-1-formylleurosidine, 4-oxo-4-desacetoxyleurosine, 4-oxo-4-desacetoxyleuroformine, 4-oxo-4-desacetoxy-4'-deoxy VLB, 4-oxo-4-desacetoxy-4'-deoxyleurosidine and the corresponding 1-formyl derivatives are prepared in similar fashion by oxidizing the corresponding 4-desacetyl compound with Moffat's Reagent or similar oxidizing agent.

The compounds of this invention are useful as intermediates for the preparation of the 4-epi-hydroxy (4α-hydroxy) derivatives of vinca alkaloids of Formula IV. Reduction of 4-desacetoxy-4-oxovinblastine, for example, with $LiAlH(t-BuO)_3$ in dry THF yields 4-desacetyl-4-epivinblastine, or 4-desacetoxy-4α-hydroxyvinblastine. This compound has shown anti-mitotic activity in transplanted tumors in mice. For example, against the Gardner lymphosarcoma, dosages of 3 and 6 mg./kg. for 10 consecutive days gave 91–100 percent inhibition of the tumor at 7 days, and against the B-16 melanoma at dosages of 3–9 mg/kg. given on days 1, 5, and 9, there was from 42 to 90 percent prolongation of life.

We claim:
1. An alkaloidal base of the formula

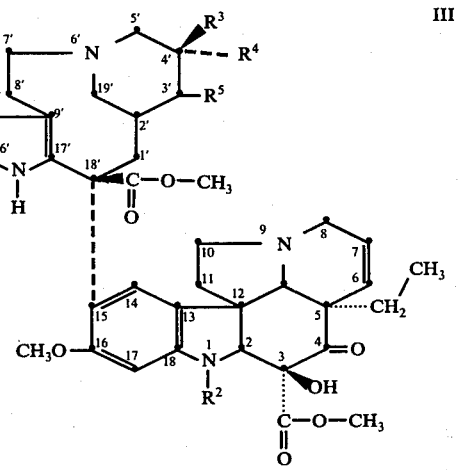

III wherein $R^2$ is $CH_3$ or CHO and when taken singly, $R^5$ is H and one of $R^3$ and $R^4$ is OH or H and the other $C_2H_5$ and when $R^4$ and $R^5$ are taken together, they form an α-epoxide ring and $R^3$ is $C_2H_5$.

2. A compound according to claim 1, in which $R^2$ is $CH_3$, $R^5$ is H, $R^3$ is OH and $R^4$ is $C_2H_5$, said compound being 4-desacetoxy-4-oxovinblastine.

* * * * *